July 15, 1958 H. CULBASHIAN Plant Pat. 1,732
APRICOT TREE
Filed Nov. 8, 1957
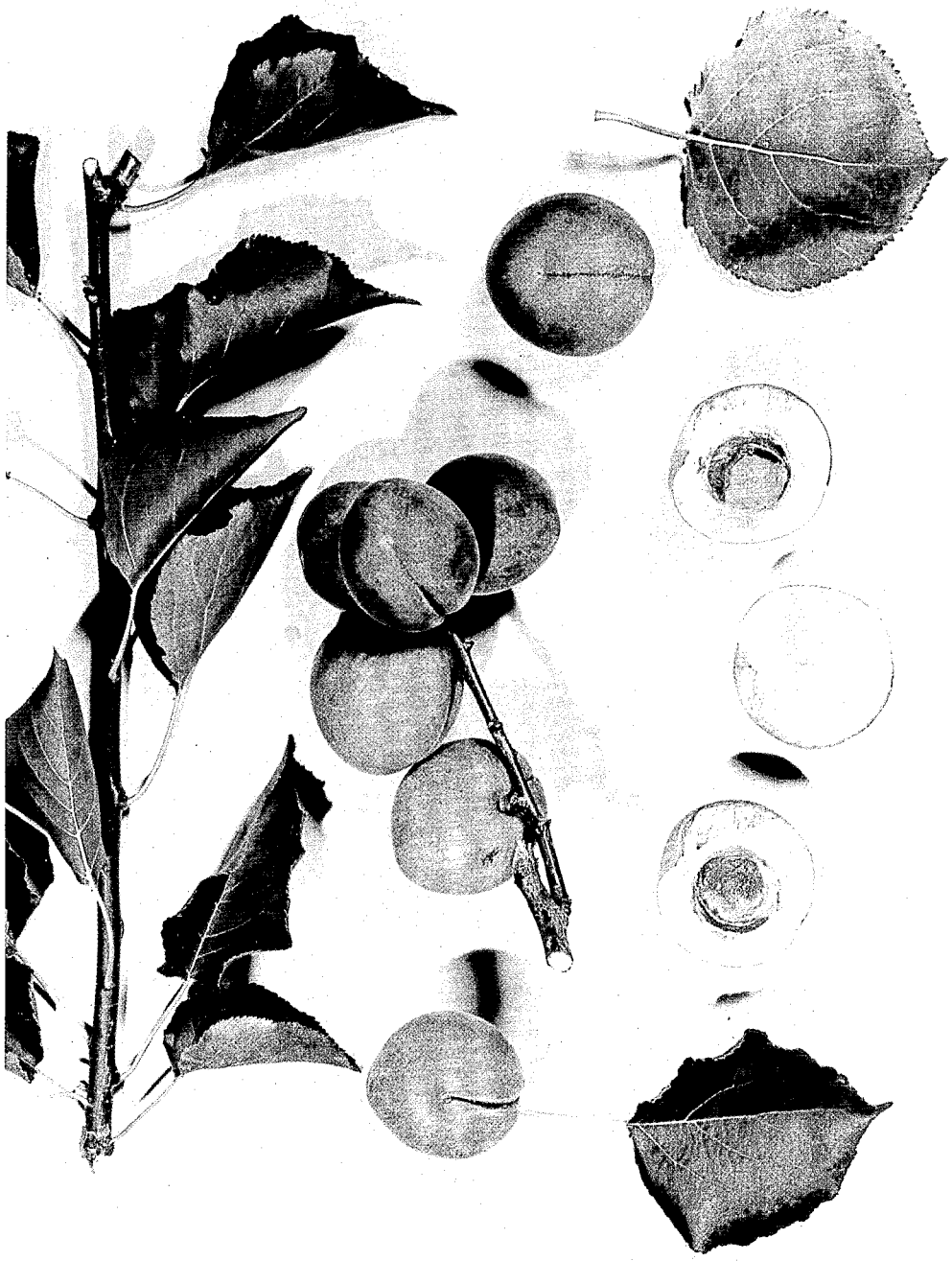
HAIG CULBASHIAN
INVENTOR
HUEBNER, BEEHLER & WORREL
ATTORNEYS
BY Richard M. Worrel United States Patent Office Plant Pat. 1,732
Patented July 15, 1958

1,732

APRICOT TREE

Haig Culbashian, Fresno, Calif.

Application November 8, 1957, Serial No. 695,473

1 Claim. (Cl. 47—62)

The present invention relates to a new and distinct variety of apricot tree.

The subject variety of apricot tree was discovered as a bud sport by me in my cultivated home orchard at 510 East Shaw Avenue, between Fresno and First Streets, near Fresno, California. While picking apricots from a tree of the Blenheim variety, unpatented, I noticed a branch on the tree bearing six apricots of distinctively dark red coloring in contrast to the brighter oranges and yellows usually associated with the Blenheim and other known apricot varieties. Continued careful observation of the branch and subsequent asexual reproduction by budding onto suitable peach seedling rootstock at my above stated home orchard established that the distinctive red color and other characteristics were successfully and consistently reproduced in the progeny of the bud sport.

In addition to its distinctive red color, the newly discovered apricot is significantly characterized by the firmness of its fruit and its good shipping characteristics; by coloring of the fruit a month to six weeks before ripening; by a flavor which is predominantly apricot but suggestive of plum; by its excellent eating quality; and by distinctive red tinge to the leaves, particularly the undersurfaces thereof.

The accompanying drawing, which is a dye transfer print of a colored photograph, shows typical specimens of the fruit and foliage of the subject apricot taken shortly after being picked near the end of June. The colors are as nearly true as is reasonably possible in a color representation of this type.

Following is a detailed description of the characteristics of the new fruit in accordance with the outline suggested by U. P. Hedrick in his book entitled "Systematic Pomology" published in 1925, and the color terminology employed as derived from the "Dictionary of Color" by Maerz and Paul, second edition.

Tree:
- *Size.*—Large.
- *Figure.*—Usual.
- *Shape.*—Usual.
- *Productivity.*—Very heavy and in this respect is similar to the parent Blenheim.

Branches:
- *Size.*—Very vigorous. As evidence of this, one year old buds in peach seedlings were budded at ground level and grew over six feet and bore fruit in the first year.
- *Surface character.*—Usual.
- *Color.*—From Kettledrum Manzanita Moro Red +, Plate 7–L–10 to Bark Mocha +, Plate 8–C–11.

Leaves:
- *Size.*—Large.
- *Average length.*—Two and seven-eighths inches.
- *Average width.*—Three and one-eighth inches.
- *Shape.*—The usual somewhat oval.
- *Color.*—Upper surface—Plate 22–J–7; lower surface background—Box Green +, Plate 22–L–3; lower surface also has a reddish tint or blush, approximating Plate 47–L–5, over the background.
- *Marginal form.*—Minutely serrated.
- *Glandular characteristics.*—Net-veined, pinnate.
- *Petiole.*—Length—one inch; thickness—one-sixteenth of an inch.

Stem glands:
- *Number.*—Singles, doubles and some triples.
- *Arrangement.*—Located on petiole on one side or both of the central vein of the leaf blade.
- *Size.*—Minute.
- *Type.*—Globose.
- *Color.*—Same as the stem.
- *Stipules.*—A pair present on each of several leaves observed.

Flower buds:
- *Size.*—Average.
- *Shape.*—No distinctive characteristics observed.
- *Other distinguishing characteristics.* — Unusually close and clustered.

Flowers:
- *Dates of blooms*—Usual, about March 1 under ecological conditions existing where grown in Fresno County of California.
- *Size.*—Somewhat smaller than usual.
- *Color.*—More pinkish than usual.

Fruit:
- *Maturity.*—Shipping ripe—the last week of June; eating ripe—the first of July.
- *Size (unpruned and unthinned).*—Uniform; average axial diameter—one and five-eighths inches; average diameter transversely in the suture plane—one and nine-sixteenths inches; average diameter transversely at right angles to the suture plane—one and five-eighths inches.
- *Form.*—Spherical; substantially symmetrical; length of the suture is usually deep and pronounced at the stem and becoming more shallow gradually toward the blossom end and appearing always to terminate at the blossom end, while the position of the suture is usual, that is, in the plane of symmetry of the fruit; rounded ventral surface; pronounced slightly conically symmetrical stem cavity of approximately three-sixteenths of an inch deep and having a mean diameter of approximately five-thirty-seconds of an inch; flat base but torus-like around the cavity; flat apex; a stem length of approximately one-fourth of an inch; and a stem caliper of approximately five-thirty-seconds of an inch.

Skin: Thickness—usual; smooth texture; no tendency to crack; color is from Plate 7–J–1 to Old Roseleaf, Plate 7–J–3; very slight pubesence or satin-like finish.

Flesh:
- *Color.*—Cadmium Y$^{P}$, Plate 9–L–8.
- *Color of pit well.*—Tan Leather Oriole, Plate 12–L–11.
- *Flavor.*—Predominantly apricot but suggestive of plum.
- *Ripening.*—Generally evenly.
- *Eating quality.*—Excellent.

Stone:
- *Type.*—Free.
- *Fibres.*—Some adherent.
- *Size.*—Approximately one inch long, fifteen-sixteenths of an inch wide, and one-half inch transversely of the suture plane.
- *Form.*—Discoidal.
- *Ridges.*—Two ridges extending approximately 180° across the surface of the stone on both sides of the suture plane and approximately 30° displaced from each other.

*Color.*—Tinsel Deep Stone, Plate 13–L–7 to Tanaura, Plate 12–D–4.

*Splitting tendency.*—None.

*Shipping quality.*—Good.

Use: Canning, freezing, drying, and fresh for shipping and local market.

Having thus described my new apricot tree, I claim:

A new and distinct variety of apricot tree, substantially as shown and described herein and especially characterized by the external deep red color of the fruit, having a flavor faintly suggestive of a plum, and by a red tinge on the under surfaces of the leaves.

No references cited.